United States Patent [19]

Rovee et al.

[11] 4,185,100

[45] Jan. 22, 1980

[54] TOPICAL ANTI-INFLAMMATORY DRUG THERAPY

[75] Inventors: David T. Rovee, Somerset; John R. Marvel; James A. Mezick, both of East Brunswick, all of N.J.

[73] Assignee: Johnson & Johnson, New Brunswick, N.J.

[21] Appl. No.: 788,453

[22] Filed: Apr. 20, 1977

Related U.S. Application Data

[63] Continuation-in-part of Ser. No. 685,942, May 13, 1976, abandoned.

[51] Int. Cl.² .................. A61K 31/38; A61K 31/56
[52] U.S. Cl. ........................... 424/240; 424/275
[58] Field of Search ........................ 424/275, 240

[56] References Cited

U.S. PATENT DOCUMENTS

| | | | |
|---|---|---|---|
| 3,243,344 | 3/1966 | Senda | 424/254 |
| 3,374,145 | 3/1968 | Enkoji et al. | 424/269 |
| 3,461,208 | 8/1969 | Winter | 424/243 |
| 3,479,396 | 11/1969 | Buu-Hoi et al. | 260/500.5 |
| 3,676,464 | 7/1972 | Foden | 260/343.6 |
| 3,721,680 | 3/1973 | Carson | 260/326.5 J |
| 3,752,826 | 8/1973 | Carson | 260/326.3 |
| 3,818,048 | 6/1974 | Foden | 260/343.6 |
| 4,012,508 | 3/1977 | Benton | 424/235 |

FOREIGN PATENT DOCUMENTS

| | | |
|---|---|---|
| 247141 | 2/1961 | Australia. |
| 2302005 | 1/1973 | Fed. Rep. of Germany. |
| 124CAM | 4/1965 | France. |
| 5944M | 4/1968 | France. |
| 1076425 | 7/1976 | United Kingdom. |

OTHER PUBLICATIONS

Fries et al., Arthritis and Rheumatism, vol. 16, No. 5, (Sep., Oct.), 1973, pp. 629–634.
Mills et al., British Med. Journal, 13 Oct. 1973, vol. 4, pp. 82–84.
Bleckman et al., J.A.M.A., Jul. 28, 1975, vol. 233, No. 4.
Glenn et al., Agents & Actions, vol. 314, (1973), pp. 210–216.
Austria Codex (1975/76), pp. 353, 397, 398, 755, 27, 182, & 392.
"Die Pharmazie", vol. 28, (1973), pp. 569–570.
FDA, vol. 17, (1973), pp. 433, 468–470.
FDA, vol. 10, (1966), pp. 139, 158, 159, 186, 187, 183–185.
Fried et al., Scand. J. Rheumatology, Supp. 2: 7–11, (1973).
C. & E.N., Dec. 10, 1956, p. 6025.
Denko et al., Proc. Soc. Exp. Biol. Med., pp. 483–484, Jul. 1957.
Floman et al., Investigative Ophthalmology & Visual Science, vol. 16, No. 1, pp. 69–73, (Jan. 1977).
Weirich et al., *Dermatologica*, 152, 87–99.
Unlisted Drugs, vol. 25, No. 4, p. 60, Apr. 1973.
Bem et al., Arch. Derm. Forsch., 251: 35–41, (1974).
Snyder et al., Brit. J. Derm. 90: 91–93, (1974).
Snyder et al., J. Invest. Derm. 62: 47–50, (1974).
Goldyne et al., Prostaglandins, 4: 737–749, (1973).
Hsia et al., Prostaglandin Synthetase Inhibitors, pp. 353–361, (1974).
Skin & Allergy News, 8 (12): 2, (1977).
Lisciani et al., Japan J. Pharmacol., 25, pp. 101–107, (1975).

*Primary Examiner*—Stanley J. Friedman
*Attorney, Agent, or Firm*—Irving Newman

[57] ABSTRACT

A pharmaceutical composition for topical treatment of cutaneous disorders or disruptions characterized by skin inflammation or hyperproliferative epidermal activity comprises the combination of a topically active anti-inflammatory corticosteroid and a non-steroidal anti-inflammatory agent which is an inhibitor of prostaglandin synthetase selected from the group consisting of the hydratropic acid derivatives; acetylsalicylic acid; the pyrazolone derivatives; the fenamic acid derivatives; the aroyl-substituted pyrroles and the substituted arylacetohydroxamic acids in a pharmaceutically acceptable topical vehicle. Treatment of above cutaneous disorders may also be effected by concurrent therapy using separate applications of corticosteroid and non-steroid.

23 Claims, No Drawings

TOPICAL ANTI-INFLAMMATORY DRUG THERAPY

CROSS-REFERENCE TO RELATED APPLICATIONS

This application is a continuation-in-part of our co-pending application Ser. No. 685,942, filed May 13, 1976, now abandoned.

BACKGROUND OF THE INVENTION

This invention relates to a pharmaceutical composition for the treatment of cutaneous disorders or disruptions characterized by skin inflammation and/or hyperproliferative activity in the epidermis. More specifically, the invention comprises treatment of such disorders by concurrent topical application to the affected area of an anti-inflammatory steroidal drug and of a selected non-steroidal anti-inflammatory drug, each in a suitable vehicle. In one preferred embodiment, the invention comprises the novel combination of an anti-inflammatory steroidal drug with a selected non-steroidal anti-inflammatory drug in a suitable vehicle for topical use.

There are many steroidal drugs suitable for treating particular responsive dermatological disorders. Many of these steroids must be used systemically. Others exhibit good activity topically in a suitable vehicle. While some steroidal anti-inflammatories are effective both systemically and topically, there is not ordinarily any predictable relationship between systemic and topical activity of a drug, particularly an anti-inflammatory steroidal drug. In addition to having a broad range of applicable biological activities (e.g., cell membrane stabilization, vasoconstrictor activity, antimitotic effect, suppression of DNA and protein synthesis, etc.), the steroids often exhibit undesired local and systemic side effects when used for prolonged periods. These may be manifested in the form of local skin atrophy, or in adrenal atrophy in the most severe case. Furthermore, a reduction in host defense mechanisms to infection may accompany their use.

Beyond the potential undesired side effects, steroids do not interact with the complete biological spectrum of inflammation. For example, ultraviolet (UV) light induced erythema is not amenable to treatment by steroidal anti-inflammatories. UV-induced early changes in skin such as vasodilatation are related to the conversion of arachidonic acid to E prostaglandins or to intermediate forms such as HETE (12L-hydroxy-5,8,10,14-eicosatetraenoic acid) or the endoperoxides which are vasoactive and are believed to have cutaneous activity, such as triggering hyperproliferative epidermal activity. See, for example, Bem, J. L. and Greaves, M. W. 1974 Prostaglandin $E_1$ effects on epidermal cell growth "in vitro." *Arch. Derm. Forsch.* 251:35–41; Snyder, D. S. and Eaglstein, W. H. 1974 Topical indomethacin and sunburn. *Brit. J. Derm.* 90:91–93; Snyder, D. S. and Eaglstein, W. H. 1974 Intradermal anti-prostaglandin agents and sunburn. *J. Invest. Derm.* 62:47–50; and Goldyne, M. E. et al. 1973 Prostaglandin activity in human cutaneous inflammation: Detection by radio-immunoassay. *Prostaglandins* 4:737–749. See also Hsia, S. L., Ziboh, V. A. and Snyder, D. S. 1974 Naturally occurring and synthetic inhibitors of prostaglandin synthetase of the skin. *Prostaglandin Synthetase Inhibitors* 353–361. Although it is not understood completely, it is thought that these effects related to prostaglandin biosynthesis are important components of many dermatopathologies, so a drug which will interfere with this biosynthesis should be useful in the clinical improvement of the disease.

There are many non-steroidal compounds or agents which also have anti-inflammatory effects. Many of these are believed to act by blocking the prostaglandin synthetase complex of enzymes that is present in normal skin and is necessary for the biosynthetic processes described above. Furthermore, as a general rule, these drugs are relatively free of unwanted side effects. Examples of such non-steroidal anti-inflammatory compounds include aspirin, indomethacin, suprofen, cliprofen and ethyl 5-p-chlorobenzoyl-1,4-dimethylpyrrole-2acetate.

DESCRIPTION OF THE INVENTION

We have discovered in the course of investigations with experimentally induced inflammation that topical treatment with a combination of certain steroidal and non-steroidal anti-inflammatory drugs results in unexpectedly improved suppression of inflammation than occurs when either drug is used alone. That is, either the combination is effective where the drugs used separately are not, or the combination provides more rapid, dramatic improvement than either drug alone, or the combination is equally effective at lower concentrations than either drug alone. This effect is postulated to result from the two drugs acting upon different aspects of the inflammatory response. Particularly in the case of UV-induced erythema, significant therapeutic effects (amelioration of the condition) are produced by combinations of the two types of drugs at concentration levels at which either drug alone has low or minimal effect. The steroid/non-steroid drug combination treatment of the present invention can also be used in the therapeutic treatment of a wide variety of dermatological disorders in which inflammation is a component. Examples of these diseases are psoriasis, eczema, contact dermatitis, atopic dermatitis, etc. Inflammation accompanying thermal or chemical burns as well as sunburn are other areas for application of the combination therapy of this invention, as are diaper rash, insect bite inflammation, gingival inflammation and pruritus. Also, vesicular diseases, especially those characterized by acantholysis, and other blistering conditions, appear to be particularly susceptible to this therapy.

In accordance with one aspect of the present invention, there is provided a topical composition for the treatment of inflammatory conditions of the skin comprising a pharmaceutically acceptable topical vehicle containing, in combination, an anti-inflammatory corticosteroid and a non-steroidal anti-inflammatory agent which is an inhibitor of prostaglandin synthetase selected from the group consisting of acetylsalicylic acid; the hydratropic acid derivatives; the pyrazolone derivatives; the fenamic acid derivatives; the aroyl-substituted pyrroles; and the substituted arylacetohydroxamic acids.

The topically useful anti-inflammatory corticosteroids are generally classified as being either halogenated or non-halogenated. Examples of suitable non-halogenated ones include hydrocortisone and its 17- and 21- esters, such as the 21-acetate and the 17-butyrate, and desonide. Examples of suitable halogenated steroids include dexamethasone, triamcinolone acetonide, fluocinolone acetonide, fluocinonide and betamethasone-17-valerate.

Suitable hydratropic acid type non-steroidal anti-inflammatory prostaglandin synthetase inhibitors that may be used in the compositions of the present invention are suprofen, cliprofen, cicloprofen, fenoprofen, flurbiprofen, ibuprofen, ketoprofen, naproxen and pirprofen. Phenylbutazone is an example of a suitable pyrazolone derivative, while flufenamic acid and mefenamic acid are examples of suitable fenamic acid derivatives. Suitable aroyl-substituted pyrroles include tolmetin as well as the other such compounds disclosed and clamied in U.S. Pat. No. 3,752,826, issued Aug. 14, 1973 to J. R. Carson, and in U.S. Pat. No. 3,721,680, issued Mar. 20, 1973 to J. R. Carson. Examples of suitable substituted arylacetohydroxamic acids include bufexemac and the other compounds disclosed and claimed in U.S. Pat. No. 3,479,396, issued Nov. 11, 1969.

The invention also provides a method of treating inflammatory conditions of the skin comprising topically applying to the affected area a composition of the present invention.

The concentrations of the active ingredients in the composition will depend upon both the particular compounds used and upon the vehicle. When triamcinolone acetonide (TA) is used in propylene glycol/ethanol (50:50 by weight), the concentration of TA should be from about 0.01% to 0.5%, preferably from about 0.05% to about 0.1%. There has been established a range of equivalency for many of the topical corticosteroids. These are known to those skilled in the art and can be determined by known methods. For example, the following equivalency has been reported: hydrocortisone, 1 percent; prednisolone and hydrocortamate, 0.5 percent; dichlorisone and methylprednisolone, 0.25 percent; fludrocortisone, dexamethasone, and triamcinolone acetonide, 0.1 percent; flurandrenolone acetonide, 0.05 percent; fluocinolone acetonide and fluorometholone, 0.025 percent; although recent studies indicate that the equipotent strengths for triamcinolone acetonide, fluocinolone acetonide, and flurandrenolone acetonide may be somewhat lower than the above approximations.

Similarly, when the non-steroid is suprofen, it is generally present in the propylene glycol/ethanol vehicle in a concentration of about 0.5% to 10%, preferably 2% to 5%; however this may vary with different non-steroidal anti-inflammatory agents. As indicated, lower or higher concentrations may be appropriate for different drugs and for other vehicles or delivery systems.

In addition to the liquid vehicles discussed above, the topical vehicle may be a cream, lotion, gel or other form acceptable for topical use.

It has further been found that inflammatory conditions of the skin may be effectively treated in accordance with the present invention by providing the concurrent therapy with separate topical compositions comprising the anti-inflammatory corticosteroid and the non-steroidal, anti-inflammatory prostaglandin synthetase inhibitor. In this embodiment, both compositions are applied to the skin at substantially the same time, i.e. one right after the other. The order of application of the drugs is not important, although the two vehicles are preferably compatible.

In general, treatment is effected by applying the composition or compositions to the affected area from one to about four times daily until the inflammation is relieved. The duration of treatment will vary with the severity of the condition, and will be about the same whether combination compositions are used or separate compositions of the different active ingredients are applied simultaneously.

TYPICAL COMBINATION FORMULATIONS
(Unless otherwise indicated, throughout this specification, all amounts are by weight.)

A. Topical Creams (oil in water emulsion type)

| Ingredients | Conc. Range (By weight) |
| --- | --- |
| Steroidal drug | 0.01–5.0 |
| Non-steroidal anti-inflammatory agent (NSAIA) | 0.5–10.0 |
| Mineral oil | 3.0–10.0 |
| Cetyl alcohol | 1.0–5.0 |
| Isopropyl myristate | 1.0–5.0 |
| Polyoxyethylene (20) stearate | 1.0–5.0 |
| Propylene glycol | 1.0–60.0 |
| Butylated hydroxyanisole | 0–0.1 |
| Benzoic acid | 0.01–0.5 |
| Sodium edetate | 0.001–0.1 |
| Purified water | q.s ad–100 |

In these oil-in-water emulsion creams, the cetyl alcohol may be replaced in whole or in part by other fats and waxes such as stearyl alcohol, glyceryl monostearate, spermaceti, white petrolatum, etc. Other emollients which may be used in place of or in addition to the mineral oil and isopropyl myristate include isopropyl palmitate, squalene, and hexadecyl alcohol. Surface-active agents other than polyoxyethylene (20) stearate may include other polyoxyethylene derivatives, sorbitan monoesters, polysorbates with suitable HLB values and other pharmaceutically acceptable surfactants known in the art. Other cosolvents which may be used in place of or in combination with the propylene glycol include glycerin, 1,2,6-hexanetriol, and the liquid polyethylene glycols (300;400). Preservatives other than benzoic acid include the parabens (methyl, propyl or combinations thereof) and sorbic acid. Antioxidants other than butylated hydroxyanisole include butylated hydroxytoluene, citric acid and propyl gallate; chelants other than sodium edetate include calcium disodium edetate and ethylenediaminetetraacetic acid (EDTA).

The following is a typical method of preparing the foregoing topical creams:

Oil Phase: Melt and dissolve mineral oil in isopropyl myristate in a suitable container (glass lined or stainless steel) heated to 80°–90° C.; then add the oil-soluble ingredients such as butylated hydroxyanisole and a portion of the surfactant, and any fats or waxes from the general formula. Continue to heat with stirring until a uniform solution/melt is obtained.

Aqueous Phase: In a separate suitable container, heat the water to 80°–90°. Then dissolve the benzoic acid and add the propylene glycol and remainder of the surfactant while mixing well.

Emulsification Step: Add the water phase to the oil phases at 80°–90° and agitate for a sufficient time period to insure complete mixing. Cool to the congealing point and add sufficient water to bring to the correct weight.

Incorporation of Active Ingredients

The non-steroidal anti-inflammatory agent can be incorporated as finely divided micronized powder or dissolved in one of the vehicle ingredients. The steroidal agent similarly can be incorporated as a micronized suspension or dissolved in a suitable solvent in the vehicle (e.g., propylene glycol).

In general, the following combinations of molecular forms of active agents can be designed to enhance the biological efficacy of the formulations:

(a) Steroid and NSAIA both present in the vehicle as solubilized species.
(b) The steroidal agent solubilized, and the NSAIA in suspension form in the vehicle.
(c) The NSAIA in solution and the steroidal agent in suspension form in the vehicle.
(d) The steroidal and non-steroidal anti-inflammatory agents partially in solution and partially in suspension forms.

B. Solutions

Liquid preparations for topical administration can be prepared in which both anti-inflammatory agents are present in solution form. These preparations can be either mainly aqueous or mainly organic, using pharmaceutically acceptable solvents, depending upon the choice of solvents and the particular anti-inflammatory agents used in the preparations. A stabilizing system, intended for maintaining the chemical integrity of the anti-inflammatory agents, may also be included if warranted. The following general formulation is illustrative:

| Ingredients | Conc. Range (By weight) |
| --- | --- |
| Steroidal agent | 0.01–5.0 |
| NSAIA | 0.5–10.0 |
| Stabilizing agent(s) | 0.0–0.2 |
| Solvent(s) | q.s. ad–100 |

The solvent system may contain one or a multiplicity of solvents suitable for topical administration, which may be selected from the lower alcohols (ethanol, isopropanol), glycols such as propylene, ethylene and polyethylene glycols (liquids at room temperature), other organic solvents such as dimethylsulfoxide, dimethylformamide, dimethylacetamide, 1,2,6-hexanetriol, butanediol and other liquid solvents completely or partially miscible with water. The stabilizing system is primarily composed of an anti-oxidant (such as butylated hydroxytoluene, butylated hydroxyanisole, propyl gallate and other compounds known to be effective and suitable for topical application) and a metal chelating agent (such as sodium edetate, mono-, -di, or tri-sodium edetate, edetate, calcium disodium edetate and other chelating agents known to be effective and suitable for topical application).

The method of preparation for these solution forms of anti-inflammatory agents is generally (as is known in the art) to dissolve the solid ingredients in the primary solvent using a suitable container (glass or stainless steel lined) and mixers. The resulting solutions can then be filtered to remove extraneous matter and brought to final weight with the co-solvent and/or primary solvent, using the customary precautions to minimize loss of solvent by evaporation.

C. Gels

The above solutions can be made into semisolid (gel) preparations by the use of gelling agents such as hydroxypropyl cellulose, hydroxyethyl cellulose, carbomer polymers, and combinations of the above, according to the following general formula and procedure.

| Ingredients | Conc. Range (By weight) |
| --- | --- |
| Steroidal agent | 0.01–5.0 |
| NSAIA | 0.5–10.0 |
| Alcohol | 10.0–70.0 |
| Co-solvent | 0–80.0 |
| Gelling agent | 0.5–5.0 |
| Purified water | q.s. ad 100 |

The gelling agent (e.g., hydroxyropyl cellulose) is added to the solution of active agent in its solvent system with agitation, while avoiding clumping or excess air entrapment, using a glass-lined or stainless steel container.

D. Ointments

Ointments (water immiscible or water miscible) of the compositions of the invention are typified by the following general formula.

| Ingredients | Conc. Range (By weight) |
| --- | --- |
| Steroidal agent | 0.01–10.0% |
| Surfactant | 0–5.0% |
| Solvent | 1.0–20% |
| White petrolatum | q.s. ad 100 |

Typically, the ointment is prepared by heating the white petrolatum in a suitable container (glass-lined or stainless steel) until fluid and adding the active ingredients in any of the following forms:

(a) a suspension, in a finely powdered, micronized state, (b) solubilized in a solvent system comprising such solvents as propylene glycol, polyethylene glycol 300, polyethylene glycol 400 or polyethylene glycol 1540 alone or in combination with 1,2,6-hexanetriol, propylene carbonate or other such solvents; with either or both of the anti-inflammatory agents solubilized. Suitable oil soluble surfactants, for example, hydroxylated lanolin, ethoxylated lanolin derivatives or polyoxyethylene esters can be added to the petrolatum to make the ointment water miscible, or the surfactants may be omitted to make the ointment water immiscible.

E. Powders

The following is a typical dusting powder formulation comprising the combination product of the invention.

| Ingredients | Conc. Range (By Weight) |
| --- | --- |
| Steroidal agent | 0.01–1.0 |
| NSAIA | 0.5–10.0 |
| Talcum powder | 0–99.49 |
| Cornstarch | 0–99.49 |

The steroidal and non-steroidal anti-inflammatory agents are mixed with the talcum powder and/or cornstarch by adding the latter in geometric progressions until the entire mixture is blended uniformly, using a glass-lined or stainless steel container and suitable mixing equipment. Particle size distributions of the anti-inflammatory agents in the range of 5–25 microns are preferred to facilitate a homogeneous mixture.

F. Aerosol

Many types of aerosol formulations can be used as vehicles for the combinations of the present invention. These can vary with the type of propellant and concentrate used in the manufacture, as is known to those skilled in the art. The example given below is for a general formula for a quick breaking alcoholic foam.

| Ingredients | Conc. Range (By Weight) |
|---|---|
| Concentrate | |
| Ethoxylated lanolin alcohol | 0.5–2.5 |
| Cetyl alcohol | 0.5–2.5 |
| Steroidal anti-inflammatory agent, micronized | 0.01–5.0 |
| Non-steroidal anti-inflammatory agent, micronized | 0.5–10.0 |
| Ethanol, USP | 30.0–90.0 |
| Distilled Water | 8.49–50.0 |
| Final Product | |
| Concentrate | 80.0–95.0 |
| Propellants 12/114, 40:60 | 5.0–20.0 |

The anti-inflammatory agents are either dissolved or dispersed in the ethanol/water solvent system together with the cetyl alcohol and the lanolin derivative. A preservative (e.g., Hyamine 1622) can be added if warranted. The concentrate is then mixed with the propellant, either by cold filling or by pressure filling according to known methods of manufacture.

G. Impregnated Tape

An adhesive tape impregnated with a combination of the anti-inflammatory agents of the invention can be prepared using the technology and directions stated in U.S. Pat. No. 3,632,740 issued on January 4, 1972 to R. C. V. Robinson et al. ("Topical Device for the Therapeutic Management of Dermatological Lesions With Steroids"). The non-steroidal anti-inflammatory agent can be added in solution in an appropriate organic solvent in a manner similar to that used for the steroidal agent.

While the foregoing discussion has been directed to the preparation of combination products, it will be apparent therefrom, as well as from the literature available to those skilled in the art, how to prepare analogous topical compositions separately containing the corticosteroid and the non-steroidal anti-inflammatory. In fact, the foregoing formulations could be used, with the simple modification of eliminating either the steroid or the non-steroidal anti-inflammatory agent. Moreover, many such separate compositions are now commercially available, at least with respect to corticosteroids.

EXAMPLE 1

The effects of a steroidal drug, triamcinolone acetonide (TA), a non-steroidal anti-inflammatory inhibitor of prostaglandin synthetase, p-(2-theonyl) hydratropic acid, suprofen(S), and the combination of the two (TA/S) were studied. The effect of the selected compositions on cutaneous inflammation caused by topical application of arachidonic acid was evaluated. In addition to inflammation, the proliferative response of the epidermis treated with arachidonic acid and the compositions was also evaluated.

For these experimental purposes, the following compositions were utilized:

| Composition No. | By Weight | Ingredient | Action |
|---|---|---|---|
| I | 0.1 | Triamcinolone acetonide | Steroidal anti-inflammatory |
| | 5 | Suprofen | NSAIA |
| | | Propylene glycol/Ethanol (50/50 by volume) | Vehicle |
| II | 0.1 | Triamcinolone acetonide | Steroidal anti-inflammatory |
| | | Propylene glycol/Ethanol (50/50) | Vehicle |
| III | 5 | Suprofen | NSAIA |
| | | Propylene glycol/ethanol (50/50) | Vehicle |
| IV | | Propylene glycol/ethanol (50/50) | Placebo (Vehicle) |

In order to ascertain the effects of compositions I - IV on arachidonic acid induced erythema, each composition had incorporated therein (in addition to the above ingredients) 1% by weight of arachidonic acid.

Erythema and hyperproliferation of guinea pig ear skin was provoked by once daily application thereto of 0.025 ml of the arachidonic acid-containing compositions (I-IV) described above, for four consecutive days. The degree of ensuing erythema was evaluated twice daily (4 and 7 hours after drug application) for the first four days and 9 a.m. on the fifth day, and graded on a 0 to 3 scale where 0=none, 1=slight, 2=moderate and 3=intense erythema. Throughout the study, tritiated thymidine, $^3$H-TdR, a radioactively labeled precursor of DNA, was administered, so that a quantitative estimate of proliferative activity could be made after the four daily treatments. The tissues were solubilized for determination of radioactivity on the fifth day. Because the labeled precursor was peculiar to DNA, the radioactivity expressed as disintegrations-per-minute-per-6 mm punch of treated skin (DPM/30 mm$^2$) allows relative comparisons of proliferative activity.

In these animal studies, it was found that the combination drug (I) was most effective in suppressing both the erythema and the proliferative response. The non-steroid alone (III) had some effect, but the steroid (II) did not appear to be active. The data summary appears in Table I.

TABLE I

| Composition | I | II | III | IV |
|---|---|---|---|---|
| No. of Guinea Pigs | 10 | 10 | 10 | 10 |
| Proliferative Response | 1443 ± 168 | 4684 ± 416 | 4076 ± 632 | 5083 ± 794 |
| Erythema (9 readings, cumulative) | 6.00 | 20.70 | 11.35 | 21.33 |
| Erythema (average) | 0.67 | 2.30 | 1.26 | 2.37 |

EXAMPLE 2

Using the same procedure and compositions as described in Example 1 above, but substituting 2% cliprofen (C) for the suprofen, the results set forth in Table II were obtained.

TABLE II

| Composition | C/TA(I) | TA(II) | C(III) | Placebo (IV) |
|---|---|---|---|---|
| No. of | | | | |

TABLE II-continued

| Composition | C/TA(I) | TA(II) | C(III) | Placebo (IV) |
|---|---|---|---|---|
| Guinea Pigs | 10 | 10 | 10 | 10 |
| Proliferative Response | 3083 ± 604 | 7497 ± 980 | 4803 ± 711 | 6930 ± 470 |
| Erythema (9 readings, cumulative) | 1.7 | 15.0 | 8.6 | 22.3 |
| Erythema (average) | 0.47 | 1.66 | 0.95 | 2.48 |

EXAMPLE 3

Using the same procedure as described in Example 1 above, but substituting 2% ethyl 5-p-chlorobenzoyl-1,4-dimethylpyrrole-2-acetate (E) for the suprofen, and substituting a mixture of 61.25% by volume DMSO and 38.75% by volume propylene glycol for the 50:50 propylene glycol:ethanol vehicle, the results set forth in Table III below were obtained.

TABLE III

| Composition | E/TA(I) | TA(II) | E(III) | Placebo (IV) |
|---|---|---|---|---|
| No. of Guinea Pigs | 10 | 10 | 10 | 10 |
| Proliferative Response | 4497 ± 411 | 7788 ± 794 | 5646 ± 780 | 6428 ± 480 |
| Erythema (9 readings, cumulative) | 12.5 | 17.4 | 17.0 | 19.9 |
| Erythema (average) | 1.39 | 1.93 | 1.89 | 2.21 |

EXAMPLE 4

Two separate cream formulations containing, respectively suprofen and triamcinolone acetonide were tested singly and in tandem to ascertain their effect on arachidonic acid induced changes in guinea pig skin.

Using a modification of the technique described in Examples 1-3, the effects of 5% by weight suprofen in Cream Base "A" and 0.1% by weight triamcinolone acetonide in Cream Base "B" on arachidonic acid induced changes in guinea pig skin were studied. In both these formulations, the drugs are present as dispersions. The base formulations are set forth below.

| Cream Base "A" | % w/w |
|---|---|
| Sorbic Acid | 0.2 |
| Isopropyl Myristate | 10.0 |
| Polyethylene (20) Stearyl ether | 2.625 |
| Polyethylene (2) Stearyl ether | 0.375 |
| Spermwax | 5.0 |
| Cetyl Alcohol | 2.5 |
| Propylene glycol | 5.0 |
| Glyceryl stearate | 10.0 |
| Purified water q.s. | 100.0 |

| Cream Base "B" | % w/w |
|---|---|
| Glyceryl Stearate | 9.44 |
| Spermaceti | 5.56 |
| Cetyl Alcohol | 2.22 |
| Isopropyl Palmitate | 2.22 |
| Polysorbate 60 | 3.33 |
| Propylene glycol | 15.0 |
| Purified water q.s. | 100.0 |

To evaluate activity of the creams, the ears of 50 guinea pigs were treated once daily for four days with a propylene glycol-ethanol (PG/EtOH)(1:1 by volume) solution of 1% by weight arachidonic acid (AA), while the contralateral ears of each animal received the PG/EtOH vehicle alone. Within 30 minutes of these applications, 0.05 cc of the test creams were applied gently to the AA treated ears. In all cases, the contralateral PG/EtOH treated ears received the appropriate cream base (no drug). The study was designed to test the effects of (1) 5% suprofen cream, (2) 0.1% triamcinolone acetonide cream, (3) tandem treatment with both the suprofen and triamcinolone acetonide creams, (4) inactive suprofen cream base, (5) inactive triamcinolone acetonide cream base. Table IV reiterates the experimental design.

TABLE IV

Experimental Design

| Group | N | Arachidonic Acid Ear | PG/EtOH (Placebo) Ear** |
|---|---|---|---|
| I | 10 | 5% S cream | cream base A |
| II | 10 | 0.1% TA cream | cream base B |
| III* | 10 | 0.1% TA + 5% S creams | cream bases B + A |
| IV | 10 | cream base A | cream base A |
| V | 10 | cream base B | cream base B |

*In this group, half the animals received TA followed by S, while the order was reversed in the other half; data were not affected by this reversal and will not be discussed further.
**Cream base A = suprofen vehicle
Cream base B = triamcinolone acetonide vehicle Throughout the four treatment days, the animals received three daily injections of $^3$H-Thymidine. Erythema was graded (0-3 scale) at 1:00 and 4:00 p.m. on the first four days, and at 9:00 a.m. on the fifth day. After the last erythema grading, the animals were killed, and six mm circular punches of dorsal skin from the central portion of the treated sites were harvested for solubilization and determination of radioactivity (DPM/6 mm punch). The total erythema was estimated for each group by plotting mean erythema grades as a function of time and measuring the areas under the curves; hence, total erythema appears in the results in "inch$^2$." The results are set forth in Table V.

TABLE V

Summary of $^3$H-TdR uptake and total erythema Induced by AA. Effects of experimental anti-inflammatory cream formulations.

| Material | N | DPM ± SE | Total Δ Erythema (inch$^2$) | Erythema |
|---|---|---|---|---|
| 1% AA/5% S cream | 10 | 4311 ± 439 | 8.6 | +0.7 |
| Placebo/cream base A | | 5419 ± 547 | 7.9 | |
| 1% AA/0.1% TA cream | 10 | 4583 ± 812 | 7.4 | +1.8 |
| Placebo/cream base B | | 5506 ± 1092 | 5.6 | |
| 1% AA/TA cream + S cream | 10 | 4096 ± 439* | 6.8 | −0.3 |
| Placebo/cream bases A + B | | 5834 ± 662 | 7.1 | |
| 1% AA/cream base A | 8** | 7279 ± 724 | 7.8 | +1.4 |
| Placebo/cream base A | | 5460 ± 771 | 6.4 | |
| 1% AA/cream base B | 10 | 7124 ± 1318 | 9.7 | +3.2 |
| Placebo/cream base B | | 5241 ± 1019 | 6.5 | |

*Only this group differs significantly from the contralateral placebo/cream bases treated ears (t = 2.674, p<0.05)
**Two animals expired due to respiratory infections unrelated to study.

Erythema, edema and $^3$H-TdR uptake data in this study are more variable than in Examples 1-3. It appears that the cream vehicles, themselves, or the application procedures may elicit an increase in $^3$H-TdR incorporation. In spite of the variability, some trends are quite apparent. It is clear that the greatest degrees of erythema occur in the two vehicle (A or B) treated groups and the TA cream group. Both the S cream and the tandem S/TA cream treatments yielded the lowest erythema scores, with the latter being best. All the placebo/cream base treated ears showed greater erythema than would be expected with an inactive placebo as judged from previous studies.

The AA-induced $^3$H-TdR uptake was clearly higher in the cream base treated groups A and B (7279±724 and 7124±1318 dpm, respectively). Furthermore, there was an apparent trend in the uptake data from the other three groups showing lowest dpm values for the S/TA creams, intermediate values for the S cream, and highest values for the TA cream. Although all three of the active cream treatments resulted in lower dpm values than the contralateral placebo/cream base treated ears, only the tandem treatment with S and TA creams resulted in a statistically significant reduction (p<0.05). These data and the erythema scores appear in Table II.

EXAMPLE 5

Following the procedure described in Example 4, a suprofen (S) gel formulation in which suprofen is solubilized was studied alone as well as in combination with 0.1% triamcinolone acetonide (TA) cream for the ability to suppress arachidonic acid (AA) induced erythema and tritiated thymidine ($^3$H-TdR) uptake. A summary of the experimental design is set forth in Table VI. The composition of the TA cream is as set forth in Example 4. The composition of the S gel is set forth below.

| Ingredient | 5% Suprofen Gel % w/w | Placebo Gel % w/w |
| --- | --- | --- |
| Suprofen | 5.0 | — |
| Klucel HF | 3.0 | 3.0 |
| Propylene Glycol | 40.0 | 40.0 |
| Ethanol (200 proof) | 30.0 | 30.0 |
| Distilled Water qs. ad | 100.0 | 100.0 |

TABLE VI

| | | Experimental Design | |
| --- | --- | --- | --- |
| Group | N | Arachidonic Acid Ear | PG/EtOH (Placebo) Ear |
| I | 10 | 5% S gel | Gel vehicle |
| II | 10 | 0.1% TA cream | Cream vehicle |
| III | 10 | S gel + TA cream | Cream + gel vehicles |
| IV | 10 | Gel vehicle | Gel vehicle |
| V | 10 | Cream vehicle | Cream vehicle |

As shown in Table VII the highest values for $^3$H-TdR uptake were seen in the gel vehicle group (IV) and the cream vehicle group (V), i.e., 9407±666 dpm's and 9904±925 dpm's, respectively. Slightly lower values were seen in the 5% S gel group (1) and the 0.1% TA cream group (II), i.e., 8211±401 dpm's and 8628±807 dpm's, respectively. All these values were significantly higher than the contralateral control ear values (p<0.05).

The 5% S gel/0.1% TA cream group (III) exhibited the lowest uptake of $^3$H-TdR (7417±863 dpm's) which also was not significantly different from the contralateral control values (7529±348 dpm's).

Total erythema expressed as areas beneath the response curves (erythema as a function of time) correlated with the $^3$H-TdR uptake results. I.e., groups IV and V showed the greatest total erythema (8.9 and 9.3 inch$^2$, respectively); groups I, II and III showed a lower response (6.2, 7.3 and 7.2 inch$^2$, respectively). Subtracting values for contralateral controls, the lowest values were seen in group III (0.2), the S gel/TA cream treated group.

TABLE VII

| | Materials | N | DPM ± SE | t-value | Total Erythema (inch$^2$) | Erythema (Δ) |
| --- | --- | --- | --- | --- | --- | --- |
| I | 5% S gel | 9* | 8211 ± 401 | 3.480 | 6.2 | +3.7 |
| | Control | | 4702 ± 508 | | 2.5 | |
| II | 0.1% TA cream | 9** | 8628 ± 807 | 3.655 | 7.3 | +3.7 |
| | Control | | 5828 ± 389 | | 3.6 | |
| III | S gel/TA cream | 10 | 7417 ± 863 | 0.119 | 7.2 | +0.2 |
| | Control | | 7529 ± 348 | | 7.0 | |
| IV | Gel Vehicle | 10 | 9407 ± 666 | 4.850 | 8.9 | +5.0 |
| | Control | | 5465± 842 | | 3.9 | |
| V | Cream vehicle | 9* | 9904 ± 925 | 3.229 | 9.3 | +3.7 |
| | Control | | 6716 ± 820 | | 5.6 | |

*One animal showed outlying value for control ear dpm's and was therefore excluded from the data.
**One animal expired due to respiratory failure unrelated to study.

EXAMPLE 6

The effects of an ointment containing a dispersion of suprofen and triamcinolone acetonide on arachidonic acid induced cutaneous reponses in guinea pigs were studied.

Following the procedure of Example 4, and as summarized in Table VIII, the ears of each animal received 0.025 ml of 1% AA or the vehicle (PG/EtOH). Within 15 minutes of these applications, the experimental ointments described below were gently applied (0.05 cc) as indicated in the previous table. These treatments were made once daily for four days during which time $^3$H-TdR was chronically administered.

TABLE VIII

| Group | N | AA-Treated Ear Skin | Vehicle-Treated Ear Skin |
|---|---|---|---|
| I | 10 | 5% suprofen (s) ointment | Placebo Ointment |
| II | 10 | 0.1% Triamcinolone acetonide (TA) ointment | " |
| III | 10 | 5% S/0.1% TA ointment | " |
| IV | 10 | Placebo ointment | " |

Experimental Ointments 1) 5% Suprofen ointment
   - 5% Suprofen — 2.5 gm
   - 5% Mineral Oil — 2.5 gm
   - 90% White Petrolatum — 45.0 gm
2) 0.1% Triamcinolone Acetonide ointment
   - 0.1% Triamcinolone acetonide — 0.050 gm
   - 2.5% Mineral Oil — 2.50 gm
   - 94.9% White Petrolatum — 47.45 gm
3) 5% Suprofen-0.1% Triamcinolone Acetonide ointment
   - 5% Suprofen — 2.5 gm
   - 0.1% Triamcinolone acetonide — 0.05 gm
   - 2.5% Mineral Oil — 2.50 gm
   - 89.9% White Petrolatum — 44.95 gm
4) Placebo Ointment
   - Mineral Oil — 2.50 gm
   - White Petrolatum — 97.5 gm Erythema was graded and plotted as a function of time (areas under response curves serve as a measure of total erythema). On the fifth day, samples were also obtained for determination of radioactivity, an indicator of $^3$H-TdR uptake.

As shown in Table IX, erythema (total) was lowest in the TA/S and S treated groups (grades of 4.74 and 5.49, respectively), and was relatively high in the TA and ointment placebo groups (6.90 and 7.12, respectively).

The greatest suppression of $^3$H-TdR uptake was seen in the S/TA ointment treated group (2857±188 dpm). The placebo ointment, 5% S ointment and 0.1% TA ointment treated groups showed higher values for $^3$H-TdR uptake (5357±542 dpm, 4881±1382 dpm, and 5609±606 dpm, respectively). The S/TA ointment group was significantly lower in radioactivity than the placebo ointment group, while the TA and S groups did not differ significantly (Student t/test, $\alpha = 0.05$).

In summary, the combination of 5% S and 0.1% TA is very effective in reducing the responses induced by topical AA.

TABLE IX

Data Summary

| Material | N | DPM ± S.E. | t-Value | Total Erythema (inch$^2$) | Erythema (Δ) |
|---|---|---|---|---|---|
| 5% S ointment + AA | | 4881 ± 1382 | | 5.49 | |
| | 10 | | 0.970 | | +0.81 |
| Placebo | | 4070 ± 996 | | 4.68 | |
| 0.1% TA ointment + AA | | 5609 ± 606 | | 7.12 | |
| | 10 | | 2.852* | | +2.22 |
| Placebo | | 3595 ± 615 | | 4.90 | |
| 5% S/0.1% TA ointment + AA | | 2857 ± 188 | | 4.74 | |
| | 10 | | −0.551 | | +0.61 |
| Placebo | | 3148 ± 554 | | 4.13 | |
| Placebo ointment + AA | | 5357 ± 542 | | 6.90 | |
| | 10 | | 5.358* | | +2.24 |
| Placebo | | 2464 ± 292 | | 4.66 | |

*Significantly higher than contralateral control ($p < 0.05$)

As will be apparent to those skilled in the art, and as indicated above, many modifications and variations of the foregoing detailed description are possible within the spirit and scope of the present invention.

Having thus described our invention, what we desire to secure by Letters Patent and hereby claimed is:

1. A method of topical treatment of an inflammatory condition of the skin comprising applying to the affected area a non-steroidal anti-inflammatory agent which is a hydratropic acid derivative selected from the group consisting of suprofen, cliprofen, cicloprofen, fenoprofen, flurbiprofen, ibuprofen, ketoprofen, naproxen and pirprofen, and, concurrently therewith, a topically active anti-inflammatory corticosteroid, each of said hydratropic acid derivative and said corticosteroid being applied in a pharmaceutically acceptable topical vehicle selected from the group consisting of creams, gels, ointments, powders, aerosols, and solutions suitable for topical administration, the amounts of said anti-inflammatory drugs being sufficient, in combination, to combat said inflammatory condition.

2. The method of claim 1 wherein said corticosteroid is selected from the group consisting of hydrocortisone, hydrocortisone 21-acetate, hydrocortisone 21-butyrate, desonide, dexamethasone, triamcinolone acetonide, fluocinolone acetonide, fluocinonide and betamethasone-17-valerate.

3. The method of claim 2 wherein said corticosteroid is triamcinolone acetonide.

4. The method of claim 1 wherein said hydratropic acid derivative is suprofen.

5. The method of claim 1 wherein said hydratropic acid derivative is cliprofen.

6. The method of claim 1 wherein said topical vehicle comprises a mixture of propylene glycol and ethanol.

7. The method of claim 1 wherein said topical vehicle comprises a mixture of propylene glycol and dimethylsulfoxide.

8. The method of claim 6 wherein said vehicle comprises approximately equal amounts by weight of said propylene glycol and said ethanol, said topically active corticosteroid comprising from about 0.01% to about 0.5% by weight of triamcinolone acetonide.

9. The method of claim 6 wherein said vehicle comprises approximately equal amounts by weight of said propylene glycol and said ethanol, said non-steroidal inhibitor of prostaglandin synthetase comprising from about 0.5% to 10% by weight of suprofen.

10. The method of claim 8 wherein said non-steroidal inhibitor of prostaglandin synthetase comprises from about 0.5% to 10% by weight of suprofen.

11. A composition for the topical treatment of an inflammatory condition of the skin comprising a pharmaceutically acceptable topical vehicle selected from the group consisting of creams, gels, ointments, powders, aerosols, and solutions suitable for topical administration, said topical vehicle containing a non-steroidal anti-inflammatory agent which is a hydratropic acid derivative selected from the group consisting of suprofen, cliprofen, cicloprofen, fenoprofen, flurbiprofen, ibuprofen, ketoprofen, naproxen and pirprofen, and a topically active anti-inflammatory corticosteroid, the amounts of said anti-inflammatory drugs being sufficient, in combination, to combat said inflammatory condition.

12. The composition of claim 11 wherein said corticosteroid is selected from the group consisting of hydrocortisone, hydrocortisone 21-acetate, hydrocortisone 21-butyrate, desonide, dexamethasone, triamcinolone acetonide, fluocinolone acetonide, fluocinonide and betamethasone-17-valerate.

13. The composition of claim 12 wherein said corticosteroid is triamcinolone acetonide.

14. The composition of claim 11 wherein said hydratropic acid derivative is suprofen.

15. The composition of claim 11 wherein said hydratropic acid derivative is cliprofen.

16. The composition of claim 11 wherein said topical vehicle comprises a mixture of propylene glycol and ethanol.

17. The composition of claim 11 wherein said topical vehicle comprises a mixture of propylene glycol and dimethylsulfoxide.

18. The composition of claim 16 wherein said vehicle comprises approximately equal amounts by weight of said propylene glycol and said ethanol, said composition comprising as the corticosteroid from about 0.01% to about 0.5% by weight of triamcinolone acetonide.

19. The composition of claim 16 wherein said vehicle comprises approximately equal amounts by weight of said propylene glycol and said ethanol, said composition comprising as the non-steroid from about 0.5% to 10% by weight of suprofen.

20. The composition of claim 18 wherein said concentration is from about 0.05% to about 0.1%.

21. The composition of claim 19 wherein said concentration is from about 2% to about 5%.

22. The composition of claim 18 which comprises as the non-steroid from about 0.5% to 10% by weight of suprofen.

23. A method of treating inflammatory conditions of the skin which comprises topically applying to the affected area the composition of claim 11.

* * * * *